United States Patent [19]

Sauli

[11] 4,076,941
[45] Feb. 28, 1978

[54] PROCESS FOR THE PREPARATION OF 1-CARBAMOYL-3-(3,5-DICHLOROPHENYL)-HYDANTOINS

[75] Inventor: Michel Sauli, Paris, France

[73] Assignee: Philagro, Lyon, France

[21] Appl. No.: 750,704

[22] Filed: Dec. 15, 1976

[30] Foreign Application Priority Data

Dec. 22, 1975 France .............................. 75 39905

[51] Int. Cl.² ........................................... C07D 233/80
[52] U.S. Cl. .................................... 548/312; 560/34
[58] Field of Search ..................... 548/312; 260/309.5

[56] References Cited

U.S. PATENT DOCUMENTS

| 2,829,157 | 4/1958 | McKinney | 260/309.5 |
| 3,755,350 | 8/1973 | Sauli | 260/309.5 |
| 3,984,430 | 10/1976 | Curran | 260/309.5 |

FOREIGN PATENT DOCUMENTS 773,529    4/1972    Belgium ........................... 260/309.5

OTHER PUBLICATIONS

Stark Biochemistry, 1965, vol. 4, pp. 2363–2367.

*Primary Examiner*—Natalie Trousof
*Attorney, Agent, or Firm*—Browdy and Neimark

[57] ABSTRACT

Fungicidal 1-carbamoyl-3-(3,5-dichlorophenyl)-hydantoins are prepared by reacting 3 mols an isocyanate of the general formula $R - N = C = O$ (wherein R is alkyl of 1–4 carbons or alkenyl of 2–4 carbons) with one mol of 3-(3,5-dichlorophenyl)-ureidoacetic acid in an anhydrous medium in the presence of an organic base.

13 Claims, No Drawings

PROCESS FOR THE PREPARATION OF 1-CARBAMOYL-3-(3,5-DICHLOROPHENYL)-HYDANTOINS

The present invention relates to a new process for the preparation of 1-carbamoyl-3-(3,5-dichlorophenyl)-hydantoins of the general formula:

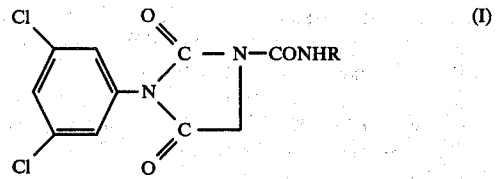

in which R represents an alkyl radical containing 1 to 4 carbon atoms in a straight or branched chain, such as isopropyl or n-propyl, or an alkenyl radical containing from 2 to 4 carbon atoms.

The products of the general formula (I), and in particular 1-isopropylcarbamoyl-3-(3,5-dichlorophenyl)-hydantoin, which possess remarkable fungicidal properties, form the subject of Belgian Pat. No. 773,529.

According to this patent, the products of the general formula (I) can be prepared by the action of an isocyanate of the general formula:

$$R - N = C = O \qquad (II)$$

in which R is defined as above, on 3-(3,5-dichlorophenyl)-hydantoin.

In general, the reaction is carried out in an inert organic solvent such as benzene, at the reflux temperature of the reaction mixture and in the presence of an organic base such as triethylamine.

3-(3,5-Dichlorophenyl)-hydantoin can be obtained by cyclisation of 3-(3,5-dichlorophenyl)-ureidoacetic acid either in an aqueous medium or in an organic medium, in the presence of a dehydrating agent.

Though this process is perfectly usable in practice, it requires two successive stages to be carried out, which from the point of view of the overall economy of the process is an obvious disadvantage, because it requires supplementary handling operations and entails losses in yield.

It has now been found, and it is this which forms the subject of the present invention, that the products of the general formula (I) can be obtained with good yields, and in a single stage, by the action of an isocyanate of the general formula (II) on 3-(3,5-dichlorophenyl)-ureidoacetic acid.

The reaction is carried out in accordance with the following equation:

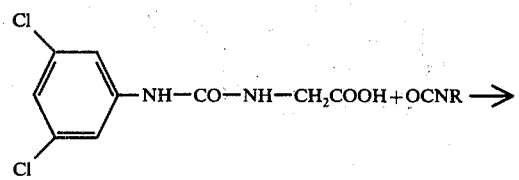

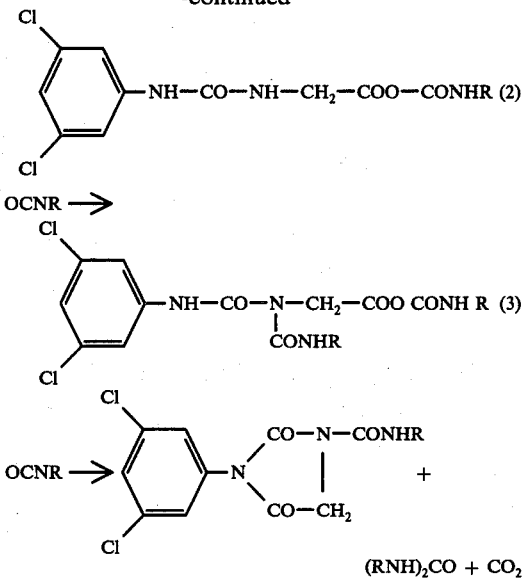

In fact, the three reactions detailed above are only given in order to emphasise the reaction mechanism, it being obvious that in reality this process takes place in a single stage by mixing the ureidoacetic acid with a suitable isocyanate.

This reaction is completely unexpected from the point of view of what was previously known about the chemistry of the isocyanates.

In fact, if reference is made to the article "Recent advances in isocyanate chemistry" by Arnold et al., published in Chemical Reviews, Vol. 57, 1957, page 47 et seq., it is found that page 52 states that the action of aliphatic or aromatic carboxylic acids on isocyanates easily gives mixed anhydrides which, depending on the strength of the starting acids, decompose more or less spontaneously into amides and $CO_2$ or, in certain cases, into anhydrides of the carboxylic acid and into disubstituted urea, with formation of $CO_2$.

Now whilst the first part of the reaction, that is to say the formation of a mixed anhydride, corresponds well to what happens in the case of the process of the present invention, the subsequent attachment of the isocyanate to the second ureido nitrogen and the subsequent cyclisation are, in contrast, completely unexpected.

As the process according to the invention employs isocyanates, the reactivity of which with water is known, it is important that the reaction should be carried out in an anhydrous medium which is chemically inert towards the starting reactants and towards the products obtained. The reaction should be carried out in the presence of an organic base.

In general, the reaction is carried out in a conventional organic solvent such as aliphatic, cycloaliphatic or aromatic solvents, and especially chlorinated solvents such as methylene chloride, dichloroethane, carbon tetrachloride, monochlorobenzene or polychlorobenzenes, aromatic hydrocarbons such as benzene, toluene and xylene, and aldehydes or ketones such as benzaldehyde, acetone, methyl isobutyl ketone and N-methylpyrrolidone.

The choice of the solvent is in fact in no way critical and essentially depends on the type of isocyanate used and on economic considerations, the local availability of a particular solvent possibly favouring the choice of this solvent in preference to another, this choice in fact having no real influence on the yield.

The temperature at which the reaction takes place can vary within wide limits between ambient temperature and the boiling point of the reaction mixture.

As it is well known that fairly generally the rate of a reaction is increased when the temperature is raised, it is of value to heat the reaction mixture to reduce the reaction time.

In general, the reaction can be carried out at between 20° and 110° and preferably between 50° and 90° C, at which temperature excellent yields are obtained for reasonable reaction times of a few hours, as emerges from the examples.

According to another characteristic of the present invention, the process of preparation according to the invention is carried out in the presence of a tertiary amine, it having been noted that tertiary amines significantly increased the rate of the reaction.

Amongst the tertiary amines which can be used in this way, there may be mentioned symmetrical or non-symmetrical trialkylamines such as trimethylamine, triethylamine, triisopropylamine and the like. The so defined amine should be present in a sufficient amount. The amount is considered as effective when its molar ratio over ureidoacetic acid is comprised between 0.5 and 1.5 and preferably between 0.75 and 1.25.

In view of the equations presented earlier, it is clear that the reaction must, in order to take place completely, be carried out by providing at least three mols of isocyanate per molecule of 3-(3,5-dichlorophenyl)-ureidoacetic acid in order to obtain as high a yield as possible.

In order to get practically interesting results, the isocyanate may be used in a molar ratio comprised between 2.9 and 4 over the ureidoacetic acid.

This latter compound is obtained by the action of 3,5-dichlorophenyl isocyanate on glycine.

The examples which follow and are given without implying a limitation, illustrate the process according to the invention applied to various isocyanates. The solvents and tertiary amines used only correspond to a possible embodiment of the process of the invention, which can be perfectly well carried out with different solvents and tertiary amines such as those described above.

EXAMPLE 1

101 g of triethylamine are added to a solution of 263 g of 2-[3-(3,5-dichlorophenyl)-ureido]-acetic acid and of 300 g of isopropyl isocyanate in 1,000 cm³ of N-methyl-pyrrolid-2-one which is heated to 70° C, and the mixture is stirred for 3 hours at 70° C. After distilling the excess isopropyl isocyanate under 20 mm of mercury and filtering off the insoluble matter, the reaction mixture is poured into 6,000 cm³ of distilled water. The precipitate formed is filtered off and dried to give 327 g of a product which melts at 132° C and which, when washed with 150 cm³ of ethanol and dried, gives 297 g of 1-isopropylcarbamoyl-3-(3,5-dichlorophenyl)-hydantoin melting at 135° C.

Yield: 82%.

EXAMPLE 2

101 g of triethylamine are added to a suspension of 263 g of 2-[3-(3,5-dichlorophenyl)-ureido]-acetic acid in 2,000 cm³ of chlorobenzene and 300 g of isopropyl isocyanate, which has been heated to 50° C, and the mixture is stirred for 4 hours at 80°–90°. After cooling, the reaction mixture is stirred for 30 minutes with 500 cm³ of a 7% strength (weight/volume) aqueous solution of hydrochloric acid. The organic solution is decanted, dried and concentrated under reduced pressure. 332 g of 1-isopropylcarbamoyl-3-(3,5-dichlorophenyl)-hydantoin melting at 130° C are thus obtained.

Yield: 91%.

EXAMPLE 3

10.1 g of triethylamine are added to a suspension of 26.3 g of 2-[3-(3,5-dichlorophenyl)-ureido]-acetic acid in 200 cm³ of chlorobenzene and 24.9 g of ethyl isocyanate, which has been heated to 50° C, and the mixture is stirred for 4 hours at 70° C. After cooling, the reaction mixture is stirred for 30 minutes with 50 cm³ of a 7% strength (weight/volume) aqueous solution of hydrochloric acid. The organic solution is decanted, dried and concentrated under reduced pressure. After washing with 50 cm³ of ethanol, 28 g of 1-ethylcarbamoyl-3-(3,5-dichlorophenyl)-hydantoin, melting at 152° C, are thus obtained.

Yield: 80%.

EXAMPLE 4

10.1 g of triethylamine are added to a suspension of 26.3 g of 2-[3-(3,5-dichlorophenyl)-ureido]-acetic acid in 200 cm³ of chlorobenzene and 29.4 g of propyl isocyanate, which has been heated to 50° C, and the mixture is stirred for 4 hours at 70° C. After cooling, the reaction mixture is stirred for 30 minutes with 50 cm³ of a 7% strength (weight/volume) aqueous solution of hydrochloric acid. The organic solution is decanted, dried and concentrated under reduced pressure. After washing with 50 cm³ of ethanol, 29 g of 1-propylcarbamoyl-3-(3,5-dichlorophenyl)-hydantoin, melting at 92° C, are thus obtained.

Yield: 80%.

EXAMPLE 5

Very close results are obtained by operating as in example 4 with the difference that the reaction is carried out in methylene chloride as solvent and at a temperature of 42° C.

EXAMPLE 6

Very close results are obtained by operating as in example 4 with the difference that the reaction is carried out in dichloroethane as solvent and at a temperature of 78° C.

EXAMPLE 7

Very close results are obtained by operating as in example 4 with the difference that the reaction is carried out in methylisobutylcetone as solvent and at a temperature of 90° C.

I claim:

1. A process for the preparation of a 1-carbamoyl-3-(3,5-dichlorophenyl)-hydantoin of the formula:

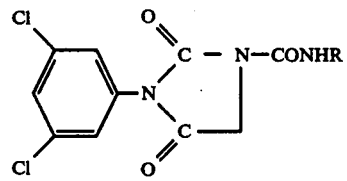

in which R represents alkyl of 1 to 4 carbon atoms in a straight or branched chain or an alkenyl of 2 to 4 carbon atoms, wherein an isocyanate of the formula:

$$R-N=C=O$$

in which R is defined as above, is reacted with 3-(3,5-dichlorophenyl)-ureidoacetic acid in an anhydrous medium in the presence of a tertiary amine capable of increasing the rate of reaction, said isocyanate being present in an amount of from 2.9 to 4 mols per mol of said ureidoacetic acid.

2. Process of preparation according to claim 1, characterised in that R is an isopropyl radical.

3. Process of preparation according to claim 1, characterised in that R is a n-propyl radical.

4. Process of preparation according to claim 1, characterised in that the anhydrous medium is an organic solvent which is chemically inert towards the starting products.

5. Process of preparation according to claim 4, characterised in that the organic solvent is a chlorinated solvent.

6. Process of preparation according to claim 5, characterised in that the organic solvent is chlorobenzene.

7. Process of preparation according to claim 4, characterised in that the organic solvent is a solvent containing a ketone group.

8. Process of preparation according to claim 7, characterised in that the organic solvent in N-methylpyrrolidone.

9. Process of preparation according to claim 1, characterised in that the reaction is carried out at a temperature of between 20° and 110° C.

10. Process of preparation according to claim 1, characterised in that the reaction is carried out at a temperature of between 50° an 90° C.

11. Process of preparation according to claim 1, characterized in that the tertiary amine is a trialkylamine.

12. Process of preparation according to claim 11, characterised in that the tertiary amine is triethylamine.

13. A process in accordance with claim 1, wherein said tertiary amine is present in an amount of 0.5 to 1.5 mols per mol of said ureidoacetic acid.

* * * * *

UNITED STATES PATENT AND TRADEMARK OFFICE
CERTIFICATE OF CORRECTION

PATENT NO. : 4,076,941
DATED : February 28, 1978
INVENTOR(S) : Michel SAULI

It is certified that error appears in the above-identified patent and that said Letters Patent are hereby corrected as shown below:

Column 3, line 62, change "82%" to --90.5%--

Column 4, line 8, change "91%" to --100%--

Column 4, line 23, change "80%" to --88.5%--

Column 4, line 38, change "80%" to --88%--

Signed and Sealed this

Sixth Day of June 1978

(SEAL)

Attest:

RUTH C. MASON
*Attesting Officer*

DONALD W. BANNER
*Commissioner of Patents and Trademarks*